United States Patent [19]

Georgiev et al.

[11] Patent Number: 4,748,264
[45] Date of Patent: May 31, 1988

[54] SUBSTITUTED ALPHA-[2'-TRICYCLO[3.3.1.1³,⁷]-DECYLIDENE]BENZENEACETONITRILE DERIVATIVES

[75] Inventors: Vassil S. Georgiev, Rochester; George B. Mullen, Avon, both of N.Y.

[73] Assignee: Pennwalt Corporation, Philadelphia, Pa.

[21] Appl. No.: 867,182

[22] Filed: May 27, 1986

[51] Int. Cl.⁴ .......................................... C07C 121/68
[52] U.S. Cl. .................................................... 558/388
[58] Field of Search ........................................ 558/388

[56] References Cited

U.S. PATENT DOCUMENTS 3,624,126  11/1971  Narayanan ..................... 260/468 B

FOREIGN PATENT DOCUMENTS 1074331  7/1967  United Kingdom .

OTHER PUBLICATIONS

CA 89:123330c, Jap. 78 19665, Yoshiaki et al., 6/22/78, "Adamantane-1-acetonitrile . . . ".
Aigami et al., "Biologically Active Polycycloalkanes.1, Antiviral Adamantane Derivatives", J. Med. Chem. 18, 713–721 (1975).
Lundahl et al., "Synthesis and Antiviral Activities of Adamantane Spiro Compounds I", J. Med. Chem. 15, 129–132 (1972).
Gaspert et al., "Synthesis of α-Amino-1-Adamantylacetic . . . Acid", Croat Chim. Acta. 48, p. 169 (1976).
Van Hes et al., "Synthesis and Antiviral Activities of Adamantane Spiro Compounds. 2", J. Med. Chem. 15, 132–136 (1972).

Primary Examiner—Anton H. Sutto

[57] ABSTRACT

Substituted α-[2'-tricyclo[3.3.1.1³,⁷]decylidene]benzeneacetonitrile derivatives having antihypoxia and anti-inflammatory activities of the formula:

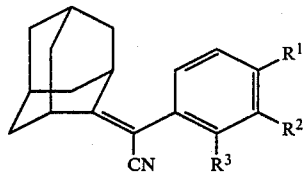

where the $R^1$, $R^2$ and $R^3$ substituents are independently selected from hydrogen, lower alkyl, lower alkoxy, halogen and trifluoromethane, provided that at least one of such substituents is hydrogen.

8 Claims, No Drawings

SUBSTITUTED ALPHA-[2'-TRICYCLO[3.3.1.1$^{3,7}$]-DECYLIDENE]-BENZENEACETONITRILE DERIVATIVES

BACKGROUND OF THE INVENTION

This invention relates generally to adamantane derivatives and more specifically to substituted α-[2'-tricyclo[3.3.1.1.$^{3,7}$]decylidene]benzeneacetonitrile derivatives.

The compounds of this invention possess useful antihypoxia activity, that is they protect warm-blooded animals from the effects of oxygen deprivation. In addition, the title compounds exerted anti-inflammatory activity when tested in the carrageenin-induced rat paw edema assay.

The ethyl 2-adamantylidenecyanoacetate (1) has been used as a precursor in the synthesis of a series of antiviral adamantane-spiro-3'-pyrrolidones (2), and α-amino-1(or 2)-adamantylacetic acids [Lundahl et al., J. Med. Chem. 15, 129 (1972) and Gaspert et al., Croat, Chim. Acta 48, 169 (1976), respectively]. The latter compounds are important in view of the fact that some synthetic penicillin analogs, with excellent antibacterial activity and resistance to penicillinase, contain an α-amino-1-adamantylmethyl side chain [Godtfredsen, Brit. Pat. No. 1,074,331 (1967)]. The conversion of 2-adamantylidenecyanoethylacetate (1) into the corresponding 2-(dicyanomethylene)adamantane (3) has also been described [Van Hes et al., J. Med. Chem. 15, 132 (1972)].

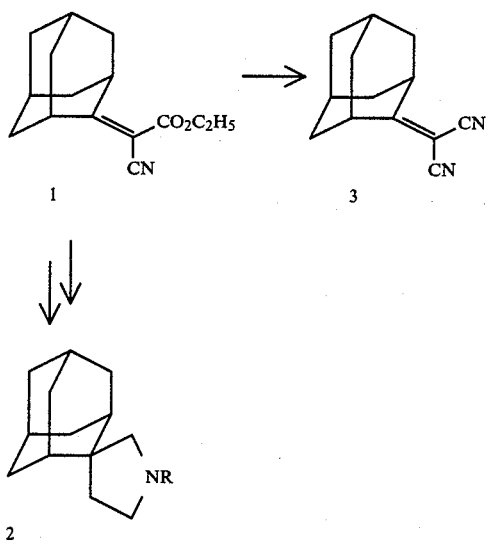

BRIEF SUMMARY OF THE INVENTION

In accordance with this invention there are provided substituted α-[2'-tricyclo[3.3.1.$^{3,7}$]decylidene]benzeneacetonitrile derivatives of the formula:

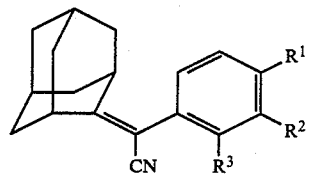

where the $R^1$, $R^2$ and $R^3$ substituents are independently selected from hydrogen, lower alkyl, lower alkoxy, halogen and trifluoromethane, provided that at least one of such substituents is hydrogen.

DETAILED DESCRIPTION

As used herein the terms "lower alkyl" and "lower alkoxy" refer to straight and branched chain alkylene groups having 1 to 4 carbons and "halogen" refers to chlorine, bromine, iodine and fluorine (preferably chlorine).

As described in the following Examples, the compounds of the invention can be prepared by the reaction of 2-adamantanone with the appropriate phenylacetonitrile as follows:

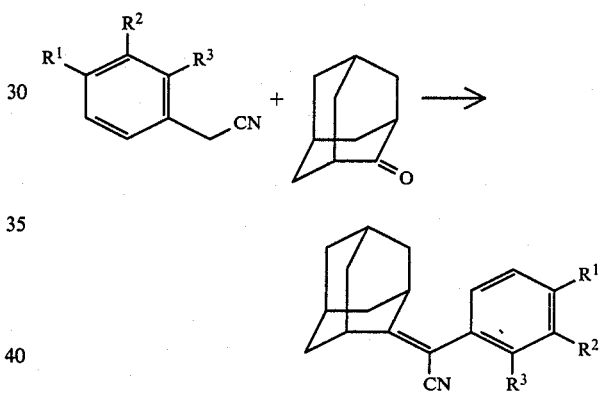

EXAMPLE 1

Preparation of α-[2'-Tricyclo[3.3.1.1$^{3,7}$]decylidene]benzeneacetonitrile

Potassium tert-butoxide (23.7 g, 0.211 mol) was dissolved in 150 ml anhydrous, ice-cold tetrahydrofuran under a nitrogen atmosphere. A solution of 24.0 ml (23.3 g, 0.209 mol) benzyl cyanide in 100 ml anhydrous tetrahydrofuran was added dropwise over 45 min to produce a dark-red solution. The ice bath was removed and a solution of 30.0 g (0.200 mol) 2-adamantanone in 200 ml anhydrous tetrahydrofuran was added over a period of 75 min. After stirring for an additional 2 hours at room temperature, the reaction mixture was poured into ice-water and extracted with ether. The organic layer was washed with water and a saturated aqueous solution of sodium chloride, then dried over MgSO$_4$. The solvent was evaporated leaving 42.59 g (85%) of α-[2'-tricyclo[3.3.1.1.$^{3,7}$]decylidene]benzeneacetonitrile. Mp 124°–127° C. (methanol).

Anal. Calcd. for C$_{18}$H$_{19}$N: C, 86.70; H, 7.68; N, 5.62. Found: C, 86.90; H, 7.63; N, 5.38.

The compounds of Examples 2–7 below were prepared according to the process of Example 1 using the appropriate phenylacetonitrile and the same molar proportions of reactants and solvents.

EXAMPLE 2

4-Chloro-α-[2'-tricyclo[3.3.1.1³,⁷]decylidene]benzeneacetonitrile

The title compound was prepared by a method similar to that described in Example 1 by reacting 4-chlorobenzeneacetonitrile ($R^1$=Cl, $R^2$=$R^3$=H) with 2-adamantanone. The compound has a melting point of 161°–163° C. (ethyl acetate).

Anal. Calcd. for $C_{18}H_{18}ClN$: C, 76.18; H, 6.39; Cl, 12.49; N, 4.94. Found: C, 75.94; H, 6.54; Cl, 12.44; N, 4.78.

EXAMPLE 3

3-Methyl-α-[2'-tricyclo[3.3.1.1³,⁷]decylidene]benzeneacetonitrile

The title compound was prepared by a method similar to that described in Example 1 by reacting 3-methylbenzene acetonitrile ($R^1$=$R^3$=H, $R^2$=$CH_3$) with 2-adamantanone. The compound has a melting point of 114°–116° C. (ethyl acetate).

Anal. Calcd. for $C_{19}H_{21}N$: C, 86.65; H, 8.04; N, 5.32. Found: C 87.18; H, 8.12; N, 5.22.

EXAMPLE 4

3-Chloro-α-[2'-tricyclo[3.3.1.1³,⁷]decylidene]benzeneacetonitrile

The title compound was prepared by a method similar to that described in Example 1 by reacting 3-chlorobenzeneacetonitrile ($R^1$=$R^3$=H, $R^2$=Cl) with 2-adamantanone. The compound has a melting point of 124°–125° C. (ethyl acetate).

Anal. Calcd. for $C_{18}H_{18}ClN$: C, 76.18; H, 6.39; Cl, 12.49; N, 4.94. Found: C, 76.34; N, 6.56; Cl, 12.76; N, 4.88.

EXAMPLE 5

3-Trifluoromethyl-α-[2'-tricyclo[3.3.1.1³,⁷]decylidene]benzeneacetonitrile

The title compound was prepared by a method similar to that described in Example 1 by reacting 3-trifluoromethylbenzeneacetonitrile ($R^1$=$R^3$=H, $R^2$=$CF_3$) with 2-adamantanone. The compound has a melting point of 134°–139° C. (methanol).

Anal. Calcd. for $C_{19}H_{18}NF_3$: C, 71.91; H, 5.72; F, 17.96; N, 4.41. Found: C, 72.42; H, 5.84; F, 17.36; N, 4.34.

EXAMPLE 6

2-Methyl-α-[2'-tricyclo[3.3.1.1³,⁷]decylidene]benzeneacetonitrile

The title compound was prepared by a method similar to that described in Example 1 by reacting 2-methylbenzeneacetonitrile ($R^1$=$R^2$=H, $R^3$=$CH_3$) with 2-adamantanone. The compound has a melting point of 134°–135° C. (ethyl acetate).

Anal. Calcd. for $C_{19}H_{21}N$: C, 86.65; H, 8.04; N, 5.32. Found: C, 86.60; H, 8.24; N, 5.18.

EXAMPLE 7

2-Methoxy-α-[2'-tricyclo[3.3.1.1³,⁷]decylidene]benzeneacetonitrile

The title compound was prepared by a method similar to that described in Example 1 by reacting 2-methoxybenzeneacetonitrile ($R^1$=$R^2$=H, $R^3$=$OCH_3$) with 2-adamantanone. The compound has a melting point of 143°–144° C. (ethyl acetate).

Anal. Calcd. for $C_{19}H_{21}NO$: C, 81.68; H, 7.58; N, 5.01. Found C, 81.96; H, 7.76; N, 4.94.

The compounds of this invention possess useful antihypoxia activity, that is, they extend the lifetime of animals exposed to a hypoxic environment. This activity is conveniently measured in mice. Groups of mice are tested at various times after the intraperitoneal administration of the test compound dissolved in saline in dosages of 1 to 100 mg/kg of mouse weight. The animals' survival time in a hypoxic environment (96% nitrogen and 4% oxygen) is recorded. A statistical comparison (Wilcoxon Rank sum) is made between coincident vehicle treated animals and the experimental group. The compounds of Examples 5 and 7 were tested at the 100 mg/kg dosage level and were found active.

When tested in the carrageenin-induced rat paw edema assay, the compounds of Example 1, 4 and 6 exerted 21.7, 25.0 and 31.3% inhibition of edema at oral doses of 50 mg/kg of rat weight, respectively, whereas the compounds of Examples 2 and 3 exerted 23.2 and 21.7% inhibition of edema at oral doses of 25 mg/kg, respectively.

We claim:
1. A compound of the formula:

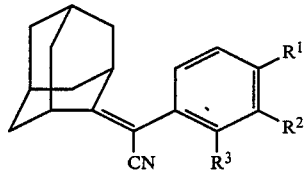

where the $R^1$, $R^2$ and $R^3$ substituents are independently selected from hydrogen, lower alkyl, lower alkoxy, halogen, and trifluoromethane provided that at least one of such substituents is hydrogen.

2. A compound according to claim 1 wherein the compound is α-[2'-tricyclo[3.3.1.1³,⁷]decylidene]benzeneacetonitrile.

3. A compound according to claim 1 wherein the compound is 4-chloro-α-[2'-tricyclo[3.3.1.1³,⁷]decylidene]benzeneacetonitrile.

4. A compound according to claim 1 wherein the compound is 3-methyl-α-[2'-tricyclo[3.3.1.1³,⁷]decylidene]benzeneacetonitrile.

5. A compound according to claim 1 wherein the compound is 3-chloro-α-[2'-tricyclo[3.3.1.1³,⁷]decylidene]benzeneacetonitrile.

6. A compound according to claim 1 wherein the compound is 3-trifluoromethyl-α-[2'-tricyclo[3.3.1.1³,⁷]decylidene]benzeneacetonitrile.

7. A compound according to claim 1 wherein the compound is 2-methyl-α-[2'-tricyclo[3.3.1.1³,⁷]decylidene]benzeneacetonitrile.

8. A compound according to claim 1 wherein the compound is 2-methoxy-α-[2'-tricyclo[3.3.1.1³,⁷]decylidene]benzeneacetonitrile.

* * * * *